United States Patent [19]

Gubitosa et al.

[11] Patent Number: 5,600,028
[45] Date of Patent: Feb. 4, 1997

[54] METHOD FOR PRODUCING LOWER POLYHYDRIC ALCOHOLS AND A NEW RUTHENIUM-BASED CATALYST USED IN THIS METHOD

[75] Inventors: Giuseppe Gubitosa, Novara; Bruno Casale, Cameri, both of Italy

[73] Assignees: Montecatini Technologie S.r.l.; Novamont S.p.A., both of Milan, Italy

[21] Appl. No.: 376,802

[22] Filed: Jan. 23, 1995

Related U.S. Application Data

[62] Division of Ser. No. 10,564, Jan. 28, 1993, Pat. No. 5,403,805.

[30] Foreign Application Priority Data

Jan. 31, 1992 [IT] Italy .................................. TO92A0079

[51] Int. Cl.$^6$ ............................ C07C 31/18; B01J 21/18; B01J 23/46
[52] U.S. Cl. ......................... 568/861; 502/183; 502/184; 502/185; 568/863
[58] Field of Search ....................... 502/183, 184, 502/185; 568/861, 863

[56] References Cited

U.S. PATENT DOCUMENTS

| | | | |
|---|---|---|---|
| 3,978,000 | 8/1976 | Schmitt, Jr. et al. | |
| 4,052,336 | 10/1977 | Van Mutfoort et al. | 502/185 |
| 4,111,842 | 9/1978 | Van Mutfoort et al. | 502/184 |
| 4,430,253 | 2/1984 | Dubeck et al. | 502/185 |
| 4,476,331 | 10/1984 | Dubeck et al. | 568/861 |
| 4,496,780 | 1/1985 | Arena | 568/861 |
| 4,560,672 | 12/1985 | Attig et al. | 502/185 |
| 5,403,805 | 4/1995 | Gubitosa et al. | 502/185 |

FOREIGN PATENT DOCUMENTS

| | | |
|---|---|---|
| 075952 | 4/1983 | European Pat. Off. . |
| 191373 | 8/1986 | European Pat. Off. . |
| 2034292 | 6/1980 | United Kingdom . |
| 2103649 | 2/1983 | United Kingdom . |

*Primary Examiner*—Asok Pal
*Attorney, Agent, or Firm*—Bryan Cave LLP

[57] ABSTRACT

A ruthenium-based hydrogenation catalyst, particularly but not exclusively for hydrogenolysis under pressure of higher polyhydric alcohols, comprises ruthenium supported on granular activated carbon, and has:

- a specific surface area of from 600 to 1000 m$^2$/g;
- a total pore volume of from 0.5 to 1.2 cm$^3$/g;
- an apparent specific weight (bulk density) of from 0.45 to 0.55 g/cm$^3$;
- an actual specific weight of from 1.9 to 2.3 g/cm$^3$;
- a total volume of micropores having a radius smaller than 75 A of from 0.4 to 0.55 cm$^3$/g; and
- an ash content of from 2 to 5% by weight.

The catalyst is used in a method for the continuous production of lower polyhydric alcohols in a fixed bed reactor, by means of hydrogenolysis under pressure of higher polyhydric alcohols.

15 Claims, No Drawings

METHOD FOR PRODUCING LOWER POLYHYDRIC ALCOHOLS AND A NEW RUTHENIUM-BASED CATALYST USED IN THIS METHOD

This is a divisional of U.S. application Ser. No. 08/010,564, filed Jan. 28, 1993, now U.S. Pat. No. 5,403,805.

The present invention relates to a method for production in a fixed bed reactor of lower polyhydric alcohols and their mixtures, comprising hydrogenolysis under pressure of higher polyhydric alcohols in the presence of a supported metal catalyst.

In the present description, the term higher polyhydric alcohols means products such as sorbitol, mannitol and xylitol derived from catalytic hydrogenation of carbohydrates (and in particular of glucose, fructose and their mixtures). The term lower polyhydric alcohols means polyalcohols having a maximum of 6 carbon atoms and a maximum of 3 hydroxyl groups, in particular ethanediol, propylene glycol, butanediol and glycerol.

The invention also relates to a new supported ruthenium-based catalyst and its use in the production of chemicals from renewable raw materials (carbohydrates and their derivatives); in particular for selective transformation of low molecular weight polyhydric alcohol hexoses.

U.S. Pat. No. 2,868,847 and U.S. Pat. No. 4,476,331 describe the use of a ruthenium-based catalyst on a powdered active carbon support. The methods of hydrogenation and catalytic hydrogenolysis described in these documents comprise batch reactions in which the powdered catalyst is supplied to the reactor together with the reagents.

A first object of the present invention is to provide a method of the type specified initially in the description, which enables hydrogenolysis of higher polyhydric alcohols to take place in a continuous fixed bed reactor.

For this purpose, a second aspect of the invention consists of use of a ruthenium-based catalyst supported on granulated activated carbon, having:

a specific surface area of 600 to 1000 m$^2$/g (B.E.T. method);
a total pore volume of 0.5 to 1.2 cm$^3$/g (combined nitrogen-mercury method);
an apparent specific weight (bulk density) of 0.45 to 0.55 g/cm$^3$;
an actual specific weight of 1.9 to 2.3 g/cm$^3$;
a total volume of micropores having a radius smaller than 75 A of 0.4 to 0.55 cm$^3$/g; and
an ash content of 2 to 5 weight %.

The specific type of activated carbon used having the aforementioned features also has high mechanical resistance and a particle size which make it suitable for use in a fixed reactor of the trickle-bed type.

The possibility of being able to carry out fixed bed hydrogenation/hydrogenolysis enables increased productivity of the plant to be obtained. It has also been found unexpectedly that fixed bed hydrogenolysis enables increased selectivity of lower polyhydric alcohols to be obtained in comparison with a reaction in batch form.

The specific surface area of the granulated activated carbon support is preferably between 800 and 1000 m$^2$/g, and the total volume of the pores is between 0.6 and 0.7 cm$^3$/g.

By granulated activated carbon is meant a carbon which has a particle size of between 5.7 and 0.5 mm (3 and 32 mesh) and preferably a particle size of between 4.7 and 2.4 mm (4 and 8 mesh, Tiller series). The optimum particle size is selected on the basis of the process parameters, according to known criteria.

Use of activated carbon which has the above-described characteristics is critical for the purposes of the activity of the catalyst and the possibility of using it on a fixed bed.

Activated carbon of the aforementioned type is available commercially in the form of the activated carbons made by ACQUE NYMCO having the references GH12132 and CA12132.

In the hydrogenolysis method according to the invention, the reaction temperature is generally between 200° and 300° C., and preferably 220°–270° C., the spatial hourly velocity of the fluid is between 0.3 and 4, and preferably between 0.67 and 2.50 h$^{-1}$, and the reaction pressure is between 5 and 20 MPa and preferably between 7.5 and 15 MPa. The continuous reactor is preferably supplied with a reaction promoter selected from amongst alkaline and alkaline earth hydroxides, and preferably sodium hydroxide, or basic reaction salts; the molar ratio between the higher polyhydric alcohols and the promoter supplied is between 3 and 30. The reactor is preferably also supplied with sulphides as reaction moderators (in order to avoid the formation of undesirable final products such as methane), with a concentration in the solution supplied lower than 150 ppm calculated relative to the sulphide ion.

The concentration of the ruthenium on the activated carbon is between 0.5 and 5 weight %, and preferably between 1 and 3 weight %.

The higher polyhydric alcohol or mixture of higher polyhydric alcohols is supplied to the hydrogenation reactor, preferably in an aqueous solution in a concentration of 20 to 40 weight %.

The higher polyhydric alcohol or mixture of higher polyhydric alcohols is preferably obtained in a first stage of hydrogenation of carbohydrates, carried out at a low basic pH and preferably between 7.5 and 8 with a reaction temperature of between 120° and 150° C. This first stage is also preferably carried out in an aqueous solution in the presence of a basic promoter, such as those previously described, in a quantity sufficient to maintain the pH in the above-described field. In this first stage the carbohydrate may consist of monosaccharides or disaccharides. However the supply preferably consists of an aqueous solution of glucose which is converted with virtually maximum theoretical yield into sorbitol. In this hydrogenation stage also, which is carried out continuously on a fixed bed, the ruthenium catalyst supported on granulated activated carbon, as previously described, is advantageously used.

The method of preparing the catalyst according to the invention comprises the main stages of suspending the granulated activated carbon in water, adding a ruthenium chloride solution to the suspension, adjusting the pH of the suspension to a value of between 4.5 and 8 by adding an alkaline agent, heating the suspension to a temperature of between 70° and 100° C. and maintaining the suspension at this temperature for a time of between 30 minutes and 2 hours, separating the solid from the suspension by filtration, re-suspending the solid in a solution of alkaline agent, heating the suspension to a temperature of between 60° and 100° C., bubbling a hydrogen flow into the suspension for a time of between 1 and 3 hours, and separating the solid from the suspension.

The catalyst thus obtained has the features of porosity, specific surface area and specific weight of the original activated carbon.

Further advantages and features of the method of producing the catalyst and of the method according to the invention which uses this catalyst will become apparent from the attached examples, which should not be understood as limitations of the scope of the present invention.

EXAMPLE 1

For preparation of the catalyst according to the present invention, an activated carbon CA 12132 of vegetable origin, and having the following characteristics, was used:
specific surface area: 800 m$^2$/g;
actual specific weight: 2.1 g/cm$^3$;
total volume of the pores: 0.6 cm$^3$/g;
micropore volume (R<75 A): 0.5 cm$^3$/g;
apparent specific weight (bulk density): 0.52 g/cm$^3$;
ash content: 3 weight
 particle size:
 10–18 mesh: (series 2–1 mm): 20–30 weight %
 18–35 mesh: (series 1–0.5 mm): 80–70 weight %.

A quantity of 303.3 g of this granulated activated carbon with 6% humidity is suspended in a liter of distilled water and is mechanically agitated. After approximately 30 minutes the pH of the suspension is 10.5. 2 liters of solution of RuCl$_3$ containing 15 g of ruthenium is added slowly to this suspension (over a period of approximately 2 hours) with a constant flow. When this addition is completed, the pH of the suspension is 0.92. The suspension is adjusted to a pH value of 4.8 by means of a 1 molar solution of sodium carbonate and after approximately 20 minutes the pH is adjusted to 6 by adding another solution, of sodium carbonate. The suspension is then heated to a temperature of 90° C. and is maintained at that temperature for approximately 2 hours. The granulated solid is separated from the solution by means of filtering, and is preliminarily washed. It is then resuspended in 2 liters of 0.1 molar solution of sodium carbonate. An argon flow is bubbled through the suspension, which is contained in a three-necked flask and is gently mechanically agitated, until the air is completely removed. The argon flow is then replaced by a hydrogen flow, and the suspension is heated to a temperature of 80° C. The suspension is maintained for 2 hours in the hydrogen flow, preferably at 80° C. The hydrogen flow is then replaced by an argon flow and the catalyst is filtered and washed until there are no chlorides in the washing waters. The wet ruthenium-based catalyst is stored in a closed container.

EXAMPLES 2–3

The catalyst prepared according to example 1 is loaded (100 cm$^3$) into a tubular, fixed, regular-flow, trickle-bed reactor provided with a gas—fluid separator disposed at the reactor outlet, a tank for supplying the reagents and a hydrogen gas tank. The reactor has a diameter of 20.5 mm (height of the catalytic bed approximately 30 cm), and is provided with a coaxial thermocouple which has 3 temperature-measuring areas disposed at 2.5, 15 and 28 cm below the upper edge of the catalytic bed. On top of the catalytic bed there is a layer of inert material(Berl Saddles)7.5 cm deep, in order to ensure that the reagents are well-mixed before coming into contact with the catalytic bed.

The reactor is closed and is connected to the system for supplying the reagents and discharging the products, and is pressurised with nitrogen in order to ensure that it is airtight. The reactor is then supplied at the test pressure with 2 flows: a mixed hydrogen—water flow, obtained by injecting water into the hydrogen current in order to saturate it, and a second flow of deionised water. Before reaching the catalytic bed, the two flows are thoroughly mixed through the layer of inert material. Heating of the reactor is then started and the test temperature is reached in approximately 2 hours. In these conditions the water flow is replaced by a flow of aqueous solution of sorbitol containing sodium hydroxide and sodium sulphide. After approximately 8 hours the temperature and spatial velocity (LHSV) of the system are steady. After this period of stabilisation two-hourly collection of the reaction products is begun. The fluid samples of-the reaction products are analysed by means of high pressure liquid chromatography (HPLC). The gas output by the gas—fluid separator is measured and analysed by means of gas chromatography, in order to reveal any hydrocarbons present (methane, ethane etc.) and the carbon dioxide. The fluid product contains mainly 1.2-propylene glycol, ethanediol, butanediol, and smaller amounts of glycerol, lactic acid and monovalent alcohols, as well as products such as erythritol, pentanediols, and possibly non-converted sorbitol. The results of examples 2–3 for two different reaction temperatures are given in tables 1 and 2 hereinafter, relative respectively to the operative conditions and distribution of the reaction products.

TABLE 1

| Example | Total pressure (bar) | Temp. (°C.) | S$^=$ supply (ppm) | Sorbitol/NaOH (molar ratio) | H$_2$/Sorb. (molar ratio) | LHSV (h$^-$) | Conversion (% sorbitol) |
| --- | --- | --- | --- | --- | --- | --- | --- |
| 2 | 150 | 250 | 600 | 3 | 6 | 1 | 100 |
| 3 | 150 | 225 | 600 | 3 | 6 | 1 | 100 |

TABLE 2

| | Distribution of the products (% carbon atoms) | | | | | | |
| --- | --- | --- | --- | --- | --- | --- | --- |
| Example | methane | monovalent alcohols | ethanediol | 1-2 propylene glycol | butanediol | glycerol | lactic acid | others |
| 2 | 0 | 5.08 | 16.50 | 41.00 | 15.00 | 1.90 | 5.20 | 15.32 |
| 3 | 0 | 1.26 | 18.00 | 49.00 | 14.10 | 2.00 | 3.67 | 12.00 |

It can be seen that a decrease in the reaction temperature gives rise to an increase in selectiveness as far as the required reaction products are concerned.

EXAMPLES 4–8

In these examples the catalyst obtained according to example 1 and the fixed bed reactor described in examples 2–3 are used, at different spatial velocities (LHSV). The results of these tests are given in tables 3 and 4 hereinafter.

TABLE 3

| Example | Total pressure (bar) | Temp. (°C.) | $S^=$ supply (ppm) | Sorbitol/NaOH (molar ratio) | $H_2$/Sorb. (molar ratio) | LHSV ($h^-$) | Conversion (% sorbitol) |
|---|---|---|---|---|---|---|---|
| 4 | 150 | 225 | 600 | 3 | 9 | 0.67 | 100 |
| 5 | 150 | 225 | 600 | 3 | 9 | 1.00 | 100 |
| 6 | 150 | 225 | 600 | 3 | 9 | 1.25 | 99.8 |
| 7 | 150 | 225 | 600 | 3 | 9 | 1.60 | 99.8 |
| 8 | 150 | 225 | 600 | 3 | 9 | 2.50 | 99.0 |

TABLE 4

| | Distribution of the products (% carbon atoms) | | | | | | | |
|---|---|---|---|---|---|---|---|---|
| Example | methane | monovalent alcohols | ethanediol | 1-2 propylene glycol | butanediol | glycerol | lactic acid | others |
| 4 | 0 | 2.8 | 17 | 46 | 14.3 | 2 | 4.43 | 13.5 |
| 5 | 0 | 1.26 | 18 | 49 | 14.1 | 2 | 3.67 | 12.0 |
| 6 | 0 | 1.54 | 18 | 48 | 13.7 | 2.3 | 3.60 | 12.9 |
| 7 | 0 | 0.84 | 18.5 | 50 | 13.22 | 4.4 | 2.90 | 10.10 |
| 8 | 0 | 1.86 | 21.0 | 51 | 13.97 | 4.5 | 3.14 | 4.55 |

EXAMPLES 9–11

These examples show the effect of the overall reaction pressure on the output of diols in the continuous fixed bed process for conversion of the sorbitol on a catalyst prepared according to example 1 and used in a reactor according to examples 2 and 3. The results of the tests are given in tables 5 and 6 hereinafter.

TABLE 5

| Example | Total pressure (bar) | Temp. (°C.) | $S^=$ supply (ppm) | Sorbitol/NaOH (molar ratio) | $H_2$/Sorb. (molar ratio) | LHSV ($h^-$) | Conversion (% sorbitol) |
|---|---|---|---|---|---|---|---|
| 9 | 150 | 250 | 600 | 3 | 6 | 1.25 | 99.8 |
| 10 | 105 | 225 | 600 | 3 | 6 | 1.25 | 99.8 |
| 11 | 75 | 225 | 600 | 3 | 6 | 1.25 | 99.2 |

TABLE 6

| | Distribution of the products (% carbon atoms) | | | | | | | |
|---|---|---|---|---|---|---|---|---|
| Example | methane | monovalent alcohols | ethanediol | 1-2 propylene glycol | butanediol | glycerol | lactic acid | others |
| 9 | 0 | 1.54 | 18 | 48 | 13.7 | 2.3 | 3.60 | 12.9 |
| 10 | 0 | 2.83 | 18 | 50 | 15.51 | 3.0 | 3.83 | 6.8 |
| 11 | 0 | 3.56 | 15 | 43 | 14.30 | 3.0 | 4.60 | 16.5 |

EXAMPLES 12–15

In these examples the catalyst prepared according to example 1 is used in a reactor according to examples 2 and 3 in a sorbitol hydrogenolysis process which varies the molar ratio between the sorbitol and promoter (NaOH) in the supply flow.

The results are given in tables 7 and 8 hereinafter.

TABLE 7

| Example | Total pressure (bar) | Temp. (°C.) | S= supply (ppm) | Sorbitol/NaOH (molar ratio) | H$_2$/Sorb. (molar ratio) | LHSV (h$^-$) | Conversion (% sorbitol) |
|---|---|---|---|---|---|---|---|
| 12 | 150 | 235 | 600 | 4 | 6 | 1.25 | 100 |
| 13 | 150 | 235 | 600 | 6 | 6 | 1.25 | 99.7 |
| 14 | 150 | 235 | 600 | 12 | 6 | 1.25 | 74.0 |
| 15 | 150 | 235 | 600 | 30 | 6 | 1.25 | 43.0 |

TABLE 8

| | Distribution of the products (% carbon atoms) | | | | | | |
|---|---|---|---|---|---|---|---|
| Example | methane | monovalent alcohols | ethanediol | 1-2 propylene glycol | butanediol | glycerol | lactic acid | others |
| 12 | 0 | 2 | 19 | 53 | 14 | 2.4 | 4 | 5.6 |
| 13 | 0 | 0.2 | 20 | 53 | 12.5 | 5.9 | 3 | 5.4 |
| 14 | 0 | 0.1 | 18 | 41 | 9.2 | 21.0 | 3 | 7.7 |
| 15 | 0 | 0 | 19 | 39 | 8.5 | 28.0 | 3.5 | 2.0 |

EXAMPLES 16–18

In these examples the catalyst prepared according to example 1 is used in a reactor according to examples 2 and 3 for hydrogenation of sorbitol, varying the sulphur ion content, the sorbitol/promoter molar ratio in the supply, and the reaction temperature.

The results are given in tables 9 and 10 hereinafter.

TABLE 9

| Example | Total pressure (bar) | Temp. (°C.) | S= supply (ppm) | Sorbitol/NaOH (molar ratio) | H$_2$/Sorb. (molar ratio) | LHSV (h$^-$) | Conversion (% sorbitol) |
|---|---|---|---|---|---|---|---|
| 16 | 100 | 235 | 115 | 6 | 6 | 1.25 | 78 |
| 17 | 100 | 235 | 115 | 6 | 6 | 1.25 | 76 |
| 18 | 100 | 235 | 0 | 3 | 6 | 1.25 | 98.5 |

TABLE 10

| | Distribution of the products (% carbon atoms) | | | | | | |
|---|---|---|---|---|---|---|---|
| Example | methane | monovalent alcohols | ethanediol | 1-2 propylene glycol | butanediol | glycerol | lactic acid | others |
| 16 | 0 | 2.5 | 17 | 44 | 12.7 | 10 | 4.0 | 9.8 |
| 17 | 0 | 2.5 | 18 | 47 | 13.5 | 11 | 4.5 | 3.5 |
| 18 | 4.5 | 1.6 | 14.5 | 40.5 | 10.0 | 8.3 | 4.8 | 15.8 |

What is claimed is:

1. A method for continuous production in a fixed bed reactor of lower polyhydric alcohols and their mixtures, comprising hydrogenolysis of higher polyhydric alcohols under pressure in the presence of a catalyst comprising from 0.5 to 5% by weight of ruthenium supported on granulated activated carbon, said catalyst having:

a specific surface area of from 600 to 1000 m$^2$/g;

a total pore volume of from 0.5 to 1.2 cm$^3$/g;

an apparent specific weight (bulk density) of from 0.45 to 0.55 g/cm$^3$;

an actual specific weight of from 1.9 to 2.3 g/cm$^3$;

a total volume of micropores having a radius smaller than 75 Å of from 0.4 to 0.55 cm$^3$/g; and an ash content of from 2 to 5% by weight.

2. A method according to claim 1, wherein the catalyst has a specific surface area of from 800 to 1000 m$^2$/g and a total pore volume of from 0.6 to 0.7 cm$^3$/g.

3. A method according to claim 1, wherein the catalyst has a particle-size distribution of 20–30% by weight of granules of between 10 and 18 mesh (2.0–1.0 mm) and 80–70% by weight of granules of between 18 and 35 mesh (1.0–0.5 mm).

4. A method according to claim 1, wherein the concentration of the ruthenium on the activated carbon is between 1 and 3% by weight.

5. A method according to claim 1, wherein the reaction temperature is between 220° and 270° C.

6. A method according to claim 1, wherein the higher polyhydric alcohols or mixture of higher polyhydric alcohols are supplied in an aqueous solution with a concentration of from 20 to 40% by weight, with a spatial velocity of the fluid supplied of between 0.3 and 4 h$^{-1}$.

7. A method according to claim 6, wherein the spatial velocity of the fluid supplied is between 0.67 and 2.50 h$^{-1}$.

8. A method according to claim 1, wherein the reaction pressure is between 7.5 and 20 MPa.

9. A method according to claim 6, wherein the supply solution comprises an alkaline or alkaline earth metal hydroxide as a reaction promoter, and the molar ratio between the higher polyhydric alcohols and the hydroxide is between 2 and 30.

10. A method according to claim 1, wherein the reactor is supplied with sulphides in a concentration of less than 150 ppm relative to the sulphide ion.

11. A method according to claim 1, wherein the higher polyhydric alcohol or mixture of higher polyhydric alcohols is the product of a first stage of hydrogenating carbohydrates in a fixed bed reactor with a low basic pH, using a catalyst comprising ruthenium in an amount from 0.5 to 5% by weight supported on active granulated carbon and having:

a specific surface area of from 600 to 1000 $m^2/g$;

a total pore volume of from 0.5 to 1.2 $cm^3/g$;

a total volume of micropores having a radius smaller than 75 Å of from 0.4 to 0.55 $cm^3/g$; and an ash content of from 2 to 5% by weight.

12. A method according to claim 11, wherein the pH in the first hydrogenation stage is between 7.5 and 8 in the presence of an alkaline or alkaline earth hydroxide.

13. A method according to claim 1, for continuous production in a fixed bed reactor of lower polyhydric alcohols and their mixtures, comprising hydrogenolysis of higher polyhydric alcohols under pressure as follows:

(a) providing a fixed-bed reactor comprising said catalyst according to claim 6, wherein said catalyst is a hydrogenation catalyst capable of catalyzing hydrogenolysis of higher polyhydric alcohols under pressure;

(b) supplying said fixed-bed reactor with a flow of an aqueous solution of a higher polyhydric alcohol, and a reaction promoter selected from the group consisting of alkaline hydroxides and alkaline earth hydroxides; and (c) collecting the reaction products from the fixed-bed reactor.

14. A method according to claim 13, wherein said flow of an aqueous solution to the fixed-bed reactor further comprises a sulphide reaction moderator in an amount lower than 150 ppm of said solution.

15. A method according to claim 13, wherein said activated carbon support is of a vegetable origin.

\* \* \* \* \*

UNITED STATES PATENT AND TRADEMARK OFFICE
CERTIFICATE OF CORRECTION

PATENT NO : 5,600,028

DATED : February 4, 1997

INVENTOR(S) : Giuseppe Gubitosa, et al.

It is certified that error appears in the above-identified patent and that said Letters Patent is hereby corrected as shown below:

Column 10, line 6: Delete "according to claim 6"

Signed and Sealed this

Twenty-first Day of April, 1998

Attest:

BRUCE LEHMAN

Attesting Officer

Commissioner of Patents and Trademarks